(12) United States Patent
Giles

(10) Patent No.: US 8,475,773 B2
(45) Date of Patent: *Jul. 2, 2013

(54) ORAL HYGIENE METHOD AND FORMULA

(75) Inventor: Brian Giles, Montecito, CA (US)

(73) Assignee: Mineral Science Co., Santa Ynez, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/507,151

(22) Filed: Jun. 9, 2012

(65) Prior Publication Data

US 2012/0258054 A1    Oct. 11, 2012

Related U.S. Application Data

(63) Continuation of application No. 11/103,826, filed on Apr. 12, 2005, now Pat. No. 8,197,797.

(60) Provisional application No. 60/561,784, filed on Apr. 12, 2004.

(51) Int. Cl.
*A61K 8/00* (2006.01)
*A61K 8/18* (2006.01)

(52) U.S. Cl.
USPC ............... 424/49; 424/52; 424/54; 424/57

(58) Field of Classification Search
None
See application file for complete search history.

(56) References Cited

U.S. PATENT DOCUMENTS

| | | | | |
|---|---|---|---|---|
| 3,691,272 A | * | 9/1972 | Asche | ............................. 424/57 |
| 3,934,002 A | | 1/1976 | Haefele | |
| 3,962,107 A | | 6/1976 | Levin et al. | |
| 3,983,252 A | * | 9/1976 | Buchalter | ..................... 514/698 |
| 4,097,604 A | | 6/1978 | Thiele | |

OTHER PUBLICATIONS

M.W. Dodds et al., "The relationship between plaque acid-anion profiles, and oral carbohydrate retention after . . . " J. Dent Res, 67(5):861-5 (1988) Abstract only.
S. Kalfas et al., "effect of pH on acid production from sorbitol in washed cell suspensions of oral bacteria," Caries Res 24(2):107-12 (1990) Abstract only.
M.W. Dodds et al., "Effects of dietary sucrose levels on pH fall and acid-anion profile in human dental plaque . . . " Arch Oral Biol, 31(8):509-12 (1986) Abstract only.
P.L. Schroeder et al., "Dental erosion and acid reflux disease," Ann Intern Med 122(11):809-15 (1995) Abstract only.
P. Lingstrom et al., "Effect of frequent consumption of starchy food items on enamel and dentin demineralization and on . . . " J Dent Res, 73(3):652-60 (1994) Abstract only.
L.M. Macpherson et al., "An invitro stimulation of the effects of chewing sugar-free and sugar-containing chewing . . . " J Dent Res, 72(10):1391-7 (1993) Abstract only.
B.G. Bibby et al., "Oral food clearance and the pH of plaque and saliva," J Am Dent Assoc, 112(3):333-7 (1986) Abstract only.

D.C. Abelson et al., "The effect of saliva on plaque pH in vivo," J Dent Res, 60(9):1634-8 (1981) Abstract only.
A. Millward et al., "Continuous monitoring of salivary flow rate and pH at the surface of the dentition following . . . " Caries Res, 31(1):44-9 (1997) Abstract only.
G.L. Hays et al., "Salivary pH while dissolving vitamin C-containing tablets," Am J Dent 5(5):269-71 (1992) Abstract only.
K. Nilner et al., "Effect of a buffering sugar-free lazenge on intraoral pH and electrochemical action," Acta Odontol Scand, 49(5):267-72 (1991) Abstract only.
F.M. Eggert et al., "The pH of gingival crevices and periodontal pockets in children, teenagers and adults," Arch Oral Biol, 36(3):233-8 (1991) Abstract only.
G. Maglis et al., "Determination of saliva pH in periodontal disease patients and a control group," Rev Dent Chile, 80(2):70-2 (1989) Abstract only.
C.M. Christensen et al., "Salivary changes in solution pH: a source of individual differences in sour taste perception," Physiol Behav, 40(2):221-7 (1987) Abstract only.
I.D. Mandel, "The role of saliva in maintaining oral homeostasis," Journal of the American Dental Association, 8(8:298 (7) (1989) Abstract only.
Lyda Associates Inc., RTM, "Dental erosion by fruit," Nutrition Research Newsletter, 9(1):6(2) (1990) Abstract only.
P.J. Moynihan et al., "A comparison of the relative acidogenic potential of infant milk and soy infant formula: a . . . , " Int J Paediatr Dent, 6(3):177-81 (1996) Abstract only.
Lyda Associates, Inc., RTM, "Dental properties of soft drinks," Nutrition Research Newsletter, 9(1:7(1) (1990) Abstract only.
C.C. Schurer-Maly et al., "Smoking and pH response to H2-receptor antagonists," Scond J Gastroenterol, 24(10):1172-8 (1989) Abstract only.
D. Birkhed et al., "pH changes in human dental plaque from lactose and milk before and after adaption," Caries Res 27(1):43-50 (1993) Abstract only.
C.J. Thomas et al., "Astringent subqualities in acids," Chem Senses, 20 (6):593-600 (1995) Abstract only.

(Continued)

*Primary Examiner* — Lezah Roberts
*Assistant Examiner* — Nannette Holloman
(74) *Attorney, Agent, or Firm* — Jeffrey A. McKinney; McKinney Law Group APC

(57) ABSTRACT

The present invention generally relates to oral compositions such as toothpastes, toothpowders, liquid dentrifices, mouthwashes, rinses, dental floss, denture cleansers, chewing gums, lozenges and the like. In particular, it relates to such oral compositions that include cesium and rubidium salts. In one aspect of the present invention, a composition for oral use is provided. The composition includes a cesium or rubidium salt and water having a surface tension ranging between 45 and 70 dynes per $cm^2$. In another aspect of the present invention, a method for improving oral hygiene in a mammal is provided. The method involves taking a volume of a solution into the mammal's mouth, where the solution includes a cesium or rubidium salt and water having a surface tension ranging between 45 and 70 dynes per $cm^2$, swishing the solution around and expelling the solution.

6 Claims, No Drawings

OTHER PUBLICATIONS

E. Bashire et al., "Site specificity of citric actid retention after an oral rinse," Caries Res, 29(6):467-9 (1995) Abstract only.

P. Vahl et al., "Examination of the pH of saliva in children and juveniles in relation to caries, gingivitis and oral hygiene," Stomatol DDR, 39(4):253-8 (1989) Abstract only.

* cited by examiner

ORAL HYGIENE METHOD AND FORMULA

This patent application is a continuation of U.S. patent application Ser. No. 11/103,826, filed Apr. 12, 2005, now U.S. Pat. No. 8,197,797 which claims priority under 35 U.S.C. 119 to U.S. Pat. Appl. Ser. No. 60/561,784, filed on Apr. 12, 2004. The referenced applications are hereby incorporated-by-reference in their entirety for all purposes.

FIELD OF THE INVENTION

The present invention generally relates to oral compositions such as toothpastes, toothpowders, liquid dentrifices, mouthwashes, rinses, denture cleansers, toothpicks, dental flosses, chewing gums, lozenges and the like. In particular, it relates to such oral compositions that include cesium and rubidium salts.

BACKGROUND OF THE INVENTION

Therapies for treating oral disease are primarily directed to active plaques, i.e., bacterial deposits on the surface of a tooth. Such therapies primarily rely on patient self-care, in the form of thorough oral hygiene. The hygiene, which is only marginally effective, typically consists of tooth brushing and interstitial hygiene using either dental floss or a toothpick.

Tooth cleaning by a dental professional removes plaque and cleans the deep periodontal pockets inaccessible through self care. If professional cleaning does not provide the desired, beneficial effect, the gums may be folded aside during a surgical procedure, which enables further access to periodontal pockets. This approach often damages cell tissues and promotes the viability of pathogens.

Chemotherapeutic agents may also be used to inhibit the formation of dental plaque. Chlorhexidine, for example, is a cationic agent used for such purposes. It has substantial drawbacks, however, as it can cause teeth staining and has an unpleasant taste.

Dental hygiene and denture preparations typically contain anti-plaque and/or anti-tartar agents, as well as antimicrobial agents Antimicrobial action may only briefly affect the formation of plaque by either reducing the colony number of bacteria in the mouth/dentures or by killing bacteria trapped in film. This procedure, however, does not reduce or eliminate the viability zone of oral pathogens to prevent further growth.

There is accordingly a need for oral compositions and methods that have prolonged, residual antimicrobial activity. The provision of such compositions and methods are objects of the present invention.

VARIOUS REFERENCES

M. W. Dodds et al., "The relationship between plaque pH, plaque acid anion profiles, and oral carbohydrate retention after ingestion of several 'reference foods' by human subjects," J. Dent Res, 67(5):861-5 (May 1988)—Abstract Only.

S. Kalfas et al, Effect of pH on acid production from sorbitol in washed cell suspensions of oral bacteria, Caries Res, 24(2):107-12 (1990)—Abstract Only.

M. W. Dodds et al., "Effects of dietary sucrose levels on pH fall and acid-anion profile in human dental plaque after a starch mouth-rinse," Arch Oral Biol, 31(8):509-12 (1986)—Abstract only.

P. L. Schroeder et al., "Dental erosion and acid reflux disease," Ann Intern Med, 122(11):809-15 (Jun. 1, 1995).

P. Lingstrom et al., "Effect of frequent consumption of starchy food items on enamel and dentin demineralization and on plaque pH in situ," J Dent Res, 73(3):652-60 (March 1994)—Abstract Only.

L. M. Macpherson et al., "An in vitro stimulation of the effects of chewing sugar-free and sugar-containing chewing gums on pH changes in dental plaque," J Dent Res, 72(10): 1391-7 (October 1993)—Abstract Only.

B. G. Bibby et al., "Oral food clearance and the pH of plaque and saliva," J Am Dent Assoc, 112(3):333-7 (March 1986)—Abstract Only.

D. C. Abelson et al., "The effect of saliva on plaque pH in vivo," J Dent Res, 60(9):1634-8 (September 1981)—Abstract Only.

A. Millward et al., "Continuous monitoring of salivary flow rate and pH at the surface of the dentition following consumption of acidic beverages," Caries Res, 31(1):44-9 (1997)—Abstract only.

G. L. Hays et al., "Salivary pH while dissolving vitamin C-containing tablets," Am J Dent, 5(5):269-71 (October 1992)—Abstract Only.

K. Nilner et al., "Effect of a buffering sugar-free lozenge on intraoral pH and electrochemical action," Acta Odontol Scand, 49(5):267-72 (October 1991)—Abstract Only.

F. M. Eggert et al., "The pH of gingival crevices and periodontal pockets in children, teenagers and adults," Arch Oral Biol, 36(3):233-8 (1991)—Abstract Only.

G. Maglis et al., "Determination of saliva pH in periodontal disease patients and a control group," Rev Dent Chile, 80(2): 70-2 (August 1989)—Abstract Only.

C. M. Christensen et al., "Salivary changes in solution pH: a source of individual differences in sour taste perception," Physiol Behav, 40(2):221-7 (1987)—Abstract Only.

I. D. Mandel, "The role of saliva in maintaining oral homeostasis," Journal of the American Dental Association, 8(8:298 (7) (1989)—Abstract Only.

Lyda Associates Inc.® 1990, "Dental erosion by fruit," Nutrition Research Newsletter, 9(1):6(2) (January 1990)—Abstract Only.

J. R. Newland, "Oral ulcers: keys to differential and definitive diagnosis," Consultant, 29(5):157(11) (May 1989).

P. J. Moynihan et al., "A comparison of the relative acidogenic potential of infant milk and soy infant formula: a plaque pH study," Int J Paediatr Dent, 6(3):177-81 (September 1996)—Abstract Only.

Jamie Talan, Newsday Newspaper Article entitled "Scientists getting nearer to knocking out cavities without using fluoride," p. D4 (January 1997).

Lyda Associates Inc.® 1990, "Dental properties of soft drinks," Nutrition Research Newsletter, 9(1:7(1) (January 1990).

C. C. Schurer-Maly et al., "Smoking and pH response to H2-receptor antagonists," Scand J Gastroenterol, 24(10):1172-8 (December 1989)—Abstract Only.

L. A. Elson et al., "The Sugar Content And The pH Of The Smoke Of Cigarette, Cigar And Pipe Tobaccos In Relation To Lung Cancer," Int J Cancer, 9(3):666-675 (1972)—Abstract Only.

D. Birkhed et al., "pH Changes in Human Dental Plaque from Lactose and Milk before and After Adaptation," Caries Res 27:43-50 (1993)—Abstract Only.

C. J. Thomas et al., "Astringent subqualities in acids," Chem Senses, 20(6):593-600 (December 1995)—Abstract Only.

E. Bashir et al., Department of Cardiology, School of Dentistry, Karolinska Institutet, Huddinge, Sweden, "Site specificity of citric acid retention after an oral rinse," Caries Res, 29(6):467-9 (1995)—Abstract Only.

The American Dietetic Association.®, Single Information Sheet, "FIG. 1. Definitions of oral health terms," (Mar. 19, 1997).

News Bites, Single Sheet, "Sports Drinks: Bad for Teeth?" HealthNews, p. 8 (Apr. 15, 1997).

Single page, "Medical Update—Heartburn and Tooth Trouble," Consumer Reports on Health, p. 106 (September 1995).

T. H. Grenby, "Comparison of the Cariostatic Effects of Calcium and Sodium Glycerophosphates in Rats," Hely. Odont. Acta, 17:54, 55 (October 1973).

A. H. Brook et al., "A Clinical Study of the Effect of Calcium Glycerophosphate," Helv. Odont. Acta, 17:55 (October 1973).

Single Sheet, last paragraph, Food Processing, p. 659.

Akademiia Nauk SSSR, Doblady, 161(1):244-247 (1965). P. Vahl et al., "Examination of the pH of saliva in children and juveniles in relation to caries, gingivitis and oral hygiene," Stomatol DDR, 39(4):253-8 (April 1989).

SUMMARY OF THE INVENTION

The present invention generally relates to oral compositions such as toothpastes, toothpowders, liquid dentrifices, mouthwashes, rinses, denture cleansers, toothpicks, dental flosses, chewing gums, lozenges and the like. In particular, it relates to such oral compositions that include cesium and rubidium salts.

In one aspect of the present invention, a composition for oral use is provided. The composition includes at least one cesium or rubidium salt and water having a surface tension ranging from 45 to 70 dynes per $cm^2$.

In another aspect of the present invention, a method for improving oral hygiene in a mammal is provided. The method involves taking a volume of a solution into the mammal's mouth, where the solution includes a cesium or rubidium salt and water having a surface tension ranging from 45 to 70 dynes per $cm^2$, swishing the solution around and either swallowing or expelling the solution.

In another aspect of the present invention, a paste for improving oral hygiene is provided. The paste includes a cesium or rubidium salt and an abrasive.

In another aspect of the present invention, a denture cleansing composition is provided. The denture cleansing composition includes a cesium or rubidium salt and an effervescence generator.

In another aspect of the present invention, a method of controlling oral fluids is provided. The method involves applying a hemostatic dental composition to an area within a mammal's mouth and subsequently applying a second composition. The second composition includes a cesium or rubidium salt and water having a surface tension ranging from 45 to 70 dynes per $cm^2$.

In another aspect of the present invention, a method for reducing inflammation within the mouth of a mammal is provided. The method involves applying a composition comprising from about 500 ppm to about 100,000 ppm, preferably about 1,000 ppm to about 10,000 ppm, of cesium or rubidium ions to the inflamed area.

DETAILED DESCRIPTION OF THE INVENTION

Definitions

Acidity and alkalinity are measured by pH, which is defined as the logarithm of the Hydrogen ion activity: $pH=-\log(H+)$. The parameter pHe is the pH on the exterior and pHi is the pH on the interior of the cell.

Examples of acidic beverages, which are included within the term "acidic ingestible" as used herein and which are commonly acidic, include beer, coffee including decaffeinated coffee, soft drinks including cola, fruit juice, tomato juice, lemonade and wine, and at least partially dehydrated versions generally with a pH below 3,3, or more specifically 3.1.

Examples of acidic foods, which are included within the term "acidic ingestible" as used herein, include tomato sauce and foods containing tomato sauce, such as spaghetti and pizza, pickles, citrus-flavored water ices and sherbets, salsa, pickled foods, and the like, generally, with a pH below 3.3 or more specifically 3.1.

As used herein, "acidic ingestible" also includes acidic medicaments. Such acidic medicaments include acid-based medicines or oral medications or dietary supplements having acidic active ingredients, excipients, vehicles or formulation ingredients. Such medicaments include, for example, analgesics or anti-inflammatories and vitamins, such as aspirin, ibuprofen and vitamin C (ascorbic acid).

An acid is a substance consisting of molecules of ions which donate protons (H+), and a base is a substance which accepts protons.

An acid-forming reaction is produced by any chemical reaction that produces a decreased ability to energize the biological system and leaves an acid residue, such as a hydrogen ion (H+). The result is localized acidosis with induced hypoxia, a major cause of a wide variety of degenerative oral diseases.

Plaque is initiated when bacteria adhered to pellicle form a proteinaceous film on the surface of teeth. The adherent bacteria metabolize dietary constituents and reproduce and aggregate to form the tenacious deposit known as plaque. Plaque generally consists of bacteria, bacterial end products such as polysaccharides, inorganic salts and salivary proteins. Plaque bacteria ferment dietary carbohydrates to organic acids further reducing the pH which dematerialize enamel resulting in tooth decay and contributed to a wide variety of acidotic, degenerative oral diseases.

Calculus is essentially plaque that has been mineralized with calcium phosphates salts. As calculus matures and hardens, it produces a stain due to adsorption of dietary chromagens. In addition to their undesirable appearance, calculus deposits at the gum line are a major contributing factor to gingivitis and periodontal diseases. Besides the hygienic and health problems resulting from plaque, the primary source of halitosis (bad breath) is the retention and subsequent degradation of dead cellular material sloughed off continuously by the normal, healthy mouth.

The term "reducing acidity" or "to reduce the acidity of" as used herein in relation to the mouth or the throat of a mammal means to raise and/or maintain the pH of a surface or a portion of the mouth or the throat or the saliva therein to or at a pH of about 6.0 or higher for up to about five hours after ingestion of an acidic substance (i.e., leading to the development of dental cavities). The surface or portion of the mouth or the throat or the saliva therein may include, by way of example and not by way of limitation, the surface or a portion of the teeth, the gums, and the back of the throat of a mammal.

When a mammal is a human, a human of any age, except an infant, is included.

Free radical: A free radical is an atom or molecule with an unpaired electron, that is, the electron is not paired with another electron in the formation of a chemical bond. Generally, this results in a molecule with a net magnetic moment, so it is paramagnetic. Free radicals tend to be unstable and they can damage other chemicals, tissues including DNA and RNA, etc.

The term "oral hygiene composition" as used herein includes, but is not limited to, dentifrices, mouthwashes, toothpowders, chewing gums, lozenges and denture cleansing formulations.

The term "ionic active agent" as used herein donates an ionic agent having anticalculus and/or antistaining properties in accordance with the invention, this undesirable staining is substantially reduced.

Introduction

Oral health can be influenced by many factors. One of the most fundamental factors is the correct function of homeostatic regulation of ionic concentrations, pH and membrane electrical potentials. It is currently known that the biochemical activities of living cells are controlled by pH and ion concentrations, and many key processes, such as energy metabolism and nerve and brain function, depend on membrane electrical potential. It is also known that ion movements, correct pH and membrane electrical potential are closely linked through the action of ion specific gates, electrogenic carriers and other ion carriers in cell and organelle membranes.

Most oral degenerative diseases, including pathogen invasion and propagation, are caused by a reduction in the pH, pHe and pHi and progress though a complex series of pathological and electro-biological changes from initial onset to full manifestation. Unfortunately, the prior art's drugs do not currently address the complexity of disease processes and the underlying causes or the mechanisms. This oftentimes makes them difficult to understand without knowing the fundamental electro-biological and electro physical mechanisms.

There are many drugs and therapies aimed at correcting specific disease symptoms that result from failure to maintain the ideal ionic physiological conditions. Preventative protection of the body from failure of homeostasis has generally been relegated largely to the realm of nutritional and lifestyle choices. The knowledge and understanding of ionic physiology enables us to provide oral formulations and methods that will make the protection of ionic homeostasis, such as minimizing the accumulation of damage within the cells, etc., accessible and convenient, resulting in profound benefits to human health.

The aberrant regulation of cellular homeostasis is a significant factor in the pathogenesis of disease onset. Raising the pH of the oral region, cellular pHe and cellular pHi reduces the excessive excitement of neurons, processes the stressful biological inflammatory complex free radical oxidative stress (such as super oxides, peroxides, oxyacids, alcohols and aldehydes), normalizes and stabilizes the ionic homeostasis, processes enzyme toxins and releases the useful molecular oxygen from its bound state. As an example, the central disorders of acute maladaptive reactions are oxygen deficit and acidity. The biochemistry of chronic and acute degenerative diseases reveals the same disorders as acute maladaptive reactions with a sub optimal pH that produces an acidic biological environment.

The biological environment of pathogens, anaerobic cells, has a narrow and specific viability zone and ORP range (hydrogen ion) limited to a narrow pH range, ranging between a pH of 5.5 to 7.1, with most infectious microorganisms ranging between 6.6 to 6.8. Healthy human oral cells, however, can exist in pH's and ORP's outside of a pathogen's viability zone. By increasing negative hydrogen ions in the circulating fluids and cells, the electrons tend to move those fluids increasing the pH toward an ORP and pH, in a range consistent with optimum physiologic aerobic metabolic functions. The optimum metabolic function and systemic pH promotes cellular function and repair through optimum electro-biological environment conductivity and oral pH ranges of 7.21 to 7.55, preferably 7.40.

Without the available electron donor's energy to reduce or eliminate the excess H+ migration into viable healthy cells and tissues, the pH of the electro-physical environment is reduced and compromised. This increases bactericidal capacity that occurs at a reduced pH and concomitantly reduces cell function; reduced pH unbalances signaling, further mounting an inflammatory response. This results in the onset and progression of oral disease. Therefore, altering or manipulating the oral region's pH, cellular pHe and pHi to an optimal or near optimal electro-physical environment provides disease resistance.

Cesium and/or Rubidium ions provide an "electron bath." Free radicals are bathed in electrons, and they are then stabilized and no longer able to induce cellular and tissue damage. The optimally functioning electro-biological oral environment has a narrow pHe range from a low pHe of 7.31 to 7.50, preferably between 7.37 and 7.42. The method and formula for oral pH increase and obtaining a reduction of the H+ migration, providing resistance to oral diseases and disease invasion, produces ionic changes in the pH, pHe, pHi, and changes the ionic chemistry of the oral cells and tissues.

The present invention discloses a method and formula that shifts the oral pH and electrophysiological environment from one that promotes a wide variety of oral diseases to a pH range that potentiates the optimum immune function. Increasing the pH promotes the elimination of the pathogen's electrophysiological environment and promotes regeneration of oral cells and tissues by inducing optimum electro-physical cellular function, reversing molecular pathology and restoring cellular electrochemical equilibrium. Secondarily, by stabilizing or reducing the oral acidosis and increasing oxygenation in the electro-biological environment, the hostile effects caused by acidosis (reduced pH) are reduced and eliminated, and optimum pH ranges are restored.

The formula and method will eliminate the oral acidification so that the physiologic optimum pH approaches optimal, or near optimal ranges, between 7.21 to 7.55, preferably 7.37 to 7.41. If pHe is close to optimum physiologic levels, metabolic function is not compromised and oral cellular regeneration and repair takes place.

Formulas and therapy, which enhance the ability of normal healthy tissues and cells to correctly regulate pH and other elements of cellular electrochemistry, and thereby reduce cell degeneration, damage and disease invasion will clearly be beneficial. Increasing cellular function will, at a minimum, delay the onset and ameliorate the effect of oral diseases (e.g., gingivitis progression to advanced periodontitis).

Cesium and rubidium are the two most alkali metals with chemical and physical characteristics similar to potassium. Potassium is the main internal caution of living cells. Potassium ion currents are central to the ionic physiology of normal viable healthy cells. Trans-membrane fluxes and cellular accumulation of cesium and rubidium ions are governed by the similar cellular mechanisms as those which govern potassium movements; however, cesium and rubidium ions move at slower rates and accumulate to different degrees. Cesium and rubidium ions are effective for the control of potassium fluxes and linked hydrogen ions and other ionic fluxes making them essential ionic elements for oral disease resistance (prophylaxis)

Objects and Advantages of the Invention

An advantage of the invention is that it prevents and reduces the formation of an oral, acidic hypoxic biochemical environment, thus ameliorating the effects of oral diseases, minimizing the damage within the cells and tissues, and lowering lifelong oral health costs.

A further advantage of the present invention is that it can be cost effectively administered as a stand alone therapy or as an effective adjunct in conjunction with a wide variety of known therapies.

An advantage of the present invention is to provide a therapeutic formula over an extended period of time to suppress infectious microorganisms—i.e., bacteria, viruses, and parasitic diseases—and reduce the effect of carcinogens to maintain optimum oral health.

A further object of the invention is to provide oral nutritional intervention, which is a composition that reduces oxidative stress by eliminating and preventing the formation of an acidic environment; it further reduces the production of free radicals.

A further object of the invention is to promote and maintain an oral pHe above 7.00, preferably ranging from a pH of 7.21 to 7.55 (briefly) for disease resistance, remission and prophylaxis.

A further object of the invention is to provide a method of treating or preventing gum disease or dental caries by oral application of compositions of the present invention.

A further object of the present invention is to provide an anti-plaque mouth rinse which includes antibacterial agents to promote the delivery to and retention of these agents in the mouth and soft tissues in the dental region of the oral cavity, thereby enhancing the antibacterial activity inhibiting the development of oral diseases and plaque.

A further object of the invention is to provide new oral hygiene compositions which substantially improve the oral, electrochemical environment, that alleviate the inflammatoric process and progression from gingivitis to periodontitis, and also restablilize teeth in their respective sockets.

A further object of the invention is to provide oral hygiene compositions which reduce the formation of active plaques on the surface of the tooth to improve oral hygiene in mammals, including man.

A further object of the invention is to provide new compositions that control oral bleeding or provide gingival tissue fluid control in conjunction with hemostatic compositions.

A further object of the invention is to provide new compositions that, after application, improve bonding surfaces of teeth for the addition of caps and algums.

These objects are attained in an anti plaque mouth rinse conducive to oral hygiene. The mouth rinse or gel composition includes an aqueous vehicle having dissolved therein antibacterial, alkaline ionic agents that penetrate teeth, tissues and gums to obtain their delivery. Retention of the agents on teeth and soft tissue in the dental region of the oral cavity of the user is further promoted, thereby inhibiting the formation of plaque.

The present invention provides an alkaline, ionic, pH manipulating formula and therapy for inhibiting acidotic activity (reduced pH) for restoration and prophylaxis of a wide variety of oral diseases. The therapy involves the administration of sufficient quantities of alkaline salts, in a suitable carrier, or in a wide variety of delivery forms that provide for suitable ionic, pH, electrochemical and electro-physiological requirements. More specifically, the treatment of mammals, and more specifically human patients, involves the administration of a therapeutically effective dose of a salt or salts of cesium and/or rubidium with supportive electrolytes, vitamins, trace minerals and other nutrients.

If a dental patient's immune system is suppressed by an acidic oral biological environment (localized reduced pH), either viral or bacterial-induced or age-related, the oral therapy described herein provides for an increase of the oral pH, cellular pHe and pHi to optimum ranges during the therapy cycle. This accordingly stimulates the patient's immune response and function to resist a wide variety of oral infections and diseases, and to obtain prophylaxis thereof. It is known to be effective to reduce levels of plaque that occurs in a reduced pH in the oral region of the mouth.

The invention discloses a mouthwash composition exhibiting plaque control/reduced staining tendencies comprising a salt or salts, preferably cesium and/or rubidium salt or salts, and having a pH of from 7.00 to 9.70, preferably 8.50 to 9.20.

According to the invention there is provided an oral hygiene composition comprising an effective amount of a water soluble ionic antimicrobial agent or an orally acceptable salt thereof, an effective amount of a substantially water soluble ionic active agent or agents or an orally pharmaceutically acceptable salt thereof, thus ensuring effective oral antimicrobial action and allowing the composition to be stored for long periods of time without deterioration. In one embodiment, the present invention provides an oral hygiene composition including an antimicrobial amount of an alkaline salt or salts containing ions of cesium and/or rubidium or a orally acceptable salt/salts thereof and an anti staining ionic active agent.

The oral composition provides for antimicrobial activity when administered. This activity reduces or eliminates the acidotic environment that promotes tooth decay. As a result, dental caries is improved and there is also simultaneous prophylaxis activity against additional tooth decay.

The oral composition may be formulated for use in any form of interdental or periodontal treatment and may be in the form of, for example, a dentifrice, mouthwash, tooth cream toothpowder, dental floss, toothpaste, chewing gum, lozenge, mouth spray or impregnated toothpicks, floss etc. Such compositions may contain conventional materials if they do not interfere with the alkaline ions mobility, such as, for example, humectants, gelling agents, abrasives, fluoride sources, desensitizing agents, flavorings, colorings, sweeteners, preservatives and structuring agents, and may also contain additional surfactants, anti-calculus agents and anti-plaque agents. Suitable additional surfactants are water-soluble organic compounds, and may be nonionic, cationic or amphoteric species throughout a suitable pH range.

Structuring agents may be used in, for example, dentifrices and gums to provide desirable textural properties and "mouth feel". Suitable agents include natural gum binders such as gum tragacanth, xanthan gum, gum karaya and gum arabic, seaweed derivatives, smectite clays such as diatomaceous earths, bentonite or hectorite, calcium apatite, carboxyvinyl polymers and water-soluble cellulose derivatives such as hydroxyethyl cellulose and sodium carboxymethyl cellulose. Improved texture may also be achieved, for example, by including colloidal magnesium and or aluminum silicate. Suitably, the structuring agent is included in an amount of from 0-5%, preferably 0-3% by weight of the oral hygiene composition.

Suitable abrasives include silica abrasives, such as hydrated silicas and silica gels, particularly silica xerogels. Alternative abrasives include alumina, insoluble metaphosphates such as insoluble sodium metaphosphate, calcium carbonate, dicalcium phosphate (in dihydrate and anhydrous forms), and calcium pyrophosphate (including beta-phase calcium). Calcium carbonate is a preferred abrasive. Abrasives are typically included in an amount of from 0-80%, preferably 0-60%, more preferably 5-25% by weight of the oral hygiene composition. The abrasives typically have an average particle size of about 0.1-30 microns, preferably about 5 to 15 microns.

Preferably, the oral compositions of the present invention include a cesium or rubidium ion source present in an amount sufficient to provide from about 500 ppm to about 100,000 ppm, preferably about 1,000 ppm to about 10,000 ppm, cesium and/or rubidium. The inclusion of rubidium and/or cesium salts is beneficial, as the corresponding cesium or rubidium ions will become incorporated into the hydroxyapatite of tooth enamel, which increases resistance of the enamel to tooth decay. Inclusion of a cesium ion source is also desirable when a polyphosphate, anti-calculus agent is included in the composition. This will provide for the inhibition of polyphosphate enzymatic hydrolysis by salivary phosphatase enzymes.

Flavoring agents may be included in the oral composition if desired, as long as they do not substantially interfere with the ionic mobility of cesium and/or rubidium. Such agents— e.g., oils of peppermint, wintergreen, sassafras and clove-are typically included to increase the palatability of a composition. Sweeting agents such as the following may also be included: D-tryptophan, dextrose, levulose, acesulfam, dihydrochalcones and sodium cyclamate. Such flavoring or sweetening agents are typically included in the oral hygiene composition in an amount from 0-5% by weight, preferably 0-2% by weight. Furthermore, coloring agents (e.g., colorants or pigments) may be added to improve the visual appearance of the composition. Suitable colorants include, without limitation, dyes such as FD & C blue No. 1, D & C yellow No. 10 and D & C yellow No. 3. A suitable and commonly used pigment is titanium dioxide, which provides a white color.

Flavoring agents may be lipophilic or hydrophilic. Lipophilic flavorants include, without limitation, wintergreen oil, oregano oil, bay leaf oil, peppermint oil, spearmint oil, clove oil, sage oil, sassafras oil, lemon oil, orange oil, anise oil, benzaldehyde, bitter almond oil, camphor, cedar leaf oil, marjoram oil, citronella oil, lavender oil, mustard oil, pine oil, pine needle oil, rosemary oil, thyme oil, cinnamon leaf oil, and mixtures thereof. Where used, lipophilic flavorants are typically included in the oral composition at a level from about 0.01%-10% by weight, preferably from about 0.05%-5.0% by weight, and more preferably from about 0.1%-3.0% by weight.

Anti-calculus agents suitable for use in compositions of the present invention are cesium and/or rubidium salts. A preferred agent is cesium carbonate. Cesium and/or rubidium compounds can be present in amounts sufficient to provide from about 500 ppm to about 100,000 ppm, preferably about 1,000 ppm to about 10,000 ppm of cesium and/or rubidium ions.

Other optional components for use in the present compositions include: antioxidants; vitamins (e.g., vitamin C and E); other anti-plaque agents (e.g., stannous salts, copper salts, and magnesium salts); pH adjusting agents; anticaries agents (e.g., urea, calcium glycerophosphate, and sodium trimetaphosphate), plant extracts; desensitizing agents for sensitive teeth (e.g., cesium nitrate and cesium citrate); and mixtures thereof.

Where the composition of the present invention is used as a mouth rinse, it is preferred that the ingredients of the aqueous solution are selected such that the composition may be ingestible, even by children. For example, the aqueous solution should be free of alcohol or other active ingredients which warrant poison control labeling or hazard labeling indicating that the composition is to be kept away from children. In a preferred mouth rinse embodiment, the ingredients of the rinse composition do not include alcohol, cetylpyridinium chloride or witch hazel (12-15% ethanol).

Where the composition of the present invention is used as a denture cleanser, it may additionally include one or more bleaching agents, effervescence generators, and chelating agents. The bleaching agent is typically an inorganic persalt. Examples bleaching agents include, without limitation, the following: alkali metal and ammonium persulphates, perborates percarbonates, perphosphates, and the alkali metal ions and alkaline earth metal peroxides (including potassium, ammonium, sodium and cesium persulphates and perborate mono- and tetrahydrates, sodium pyrophosphate peroxyhydrate and magnesium, calcium, and zinc peroxides and mixtures thereof).

The denture cleansing compositions can also incorporate an effervescence generator, i.e. a material which in the presence of water releases carbon dioxide or oxygen with effervescence. The effervescence generator can be selected from generators which are effective under acid, neutral or alkaline pH conditions, consisting of a combination of a generator which is effective or most effective under acid or neutral pH conditions and a generator which is effective or most effective under alkaline pH conditions. Effervescence generators that are effective under acid or neutral pH conditions include a combination of at least one alkali metal carbonate or bicarbonate, such as sodium bicarbonate, sodium carbonate, sodium sesquicarbonate, potassium carbonate, potassium bicarbonate, germanium sesquaoxide or mixtures thereof, in admixture with at least one non-toxic, physiologically-acceptable organic acid, such as but not limited to tartaric, fumaric, citric, malic, maleic, gluconic, succinic, salicylic, adipic or sulphamic acid, sodium fumarate, sodium or potassium acid phosphates.

In denture cleansing compositions in tablet form, the effervescence generator takes the form of a solid base material which in the presence of water releases carbon dioxide or oxygen with effervescence. Suitably, the solid base material incorporates a (bi) carbonate/acid effervescent couple optionally in combination with a perborate/persulphate oxygen effervescence generator. The combination of generators is valuable for achieving optimum dissolution characteristics and pH conditions for achieving optimum cleaning and antimicrobial activity. The (bi) carbonate components generally comprise from about 5% to about 65%, preferably from about 25% to 55% of the total composition; the acid components generally comprise from about 5% to about 50%, preferably from about 10% to about 30% of the total composition.

Preferred from the viewpoint of optimum dissolution and pH characteristics are bleach precursor agglomerates which comprise from about 10% to about 75%, preferably from about 20% to about 60% by weight thereof of peroxyacid bleach precursor, from about 5% to about 60% preferably from about 5% to about 50%, more preferably from about 10% to about 40% of a (bi)carbonate/acid effervescent couple, from about 0% to about 20% of a peroxoborate, and from about 5% to about 40%, preferably from about 10% to about 30% of an agglomerating agent. The final bleach precursor granules desirably have an average particle size of from about 500 to about 1500, preferably from about 500 to about 1,000μ, this being valuable from the viewpoint of optimum dissolution performance and associated aesthetics. The level of bleach precursor agglomerates, moreover, is preferably from about 1% to about 20%, more preferably from about 5% to about 15% by weight of composition.

The denture cleansing compositions of the invention can be in paste, tablet, granular or powder form, although tablet-form compositions are preferred herein. Compositions in tablet form can be single or multiple layered tablets.

Denture cleansing compositions of the invention can be supplemented by components such as surfactants, chelating agents, enzymes, flavorants, physiological cooling agents, antimicrobial compounds, dyestuffs, sweeteners, tablet binders and fillers, foam depressants (e.g., dimethylpolysiloxanes), foam stabilizers (e.g., fatty acid sugar esters), preservatives, lubricants (e.g., talc), magnesium stearate, finely divided amorphous pyrogenic silicas, etc. The free moisture content of the final composition is desirably less than about 1% and especially less than about 0.5%.

Chelating agents beneficially aid cleaning and bleach stability by keeping metal ions, such as calcium, potassium, magnesium, and heavy metal cations, in solution. Examples of suitable chelating agents may include sodium tripolyphosphate, calcium EDTA, germanium sesquaoxide, sodium acid pyrophosphate, tetrasodium pyrophosphate, aminopolycarboxylates (e.g., nitrilotriacetic acid and ethylenediamine tetracetic acid and salts thereof), and polyphosphonates and aminopolyphosphonates (e.g., hydroxyethanediphosphonic acid and salts thereof).

The chelating agent selected must be compatible with the active ionic ingredients of the denture cleanser when in the dry state and in aqueous solution. Advantageously, the chelating agent comprises between 0.1 and 60 percent by weight of the composition and preferably between 0.5 and 30 percent. Phosphonic acid chelating agents, however, preferably comprise from about 0.1 to about 1 percent, preferably from about 0.1% to about 0.5% by weight of composition.

Compositions of the present invention may also be used in conjunction with hemostatic dental compositions. The compositions are typically applied after the hemostatic compositions in the form of a liquid, a paste, a gel, an impregnated fabric strip (e.g., bandage) or an impregnated surgical sponge. The compositions preferably include either a cesium or a rubidium salt, preferably cesium chloride, cesium malate, cesium sulfate, and cesium nitrate.

Hemostatic compositions used with compositions of the present invention may include agents such as aluminum chloride, aluminum ammonium sulfate, ferric sulfate, oxidized regenerated cellulose (e.g., Surgicel™. from Johnson and Johnson), and absorbably gelatin (e.g., GELFOAM®. from UpJohn). Preferred hemostatic agents are aluminum chloride and aluminum ammonium sulfate.

The combination of hemostatic dental compositions and compositions of the present invention stop oral bleeding and provide gingival tissue fluid control without opening up the dentinal tubules in dentin. Furthermore, by using the subject compositions during dental restorative and reconstructive procedures, bleeding can be stopped so that an accurate impression for a dental prosthetic can be made. The conformational tolerance of the impression mold is significantly increased.

Any combination of cesium and/or rubidium salts which disassociate and ionize may be employed in the composition of the present invention, including,but not limited to: Arginate, Ascorbate, Caprylate, Chloride, Cysteinate, Citrate, Fumarate, Humic, Fulvate, Methionine, Glutamate, Gluconate, Glycinate, Aspartate, Lysinate, Succinate, Carbonate, Lactate, Malate, Tartrate, Chloride, Sulfate, Phosphate, Nitrate, Fluoride, Bromide, Iodide, Orotate.

Additionally, other cesium and rubidium salts might be used in a wide variety of compositions, such as, but not limited to, various organic or metallic salts, if they meet the following requirements: (1) they must be pharmaceutically acceptable and have an acceptably low level of toxicity; (2) they must have sufficiently high levels of cationic (alkaline) dissociation to allow the remaining negatively charged ions to effectively reduce the oral cavity acidity, including tissues.

The salts included in the composition of the present invention may be formed using a wide variety of acids, including, but not limited to: hydrochloric, humic, fulvic, sulfuric, acetic, lactic, tartaric, malic, succinic, etc. Ortho acids are preferred; more preferably, malic acid and citric acid are preferred acids.

Potentiation of cesium and/or rubidium ionic action can be accomplished by inclusion of ingredients that enhance ionic pH physiology. Examples are electrolytes (saline compounds) such as potassium, sodium, and magnesium. Potassium, and other major electrolytes (e.g., sodium, calcium, chloride, bicarbonate, phosphate, and sulfates) are added to the formulation in proportion to the potassium.

Other ingredients that may be included to potentiate the activity of cesium/rubidium ionic action include manganese, zinc, boron, vitamin B2, B12 (cyanocbalamin), and B6 (pyrodoxine).

The water used in the manufacture of end-product compositions of the present invention may be from any suitable source. A preferred method of manufacture is to use water processed by means such as E.C.A. (electrolytic chemical activation) processing. The method produces aqueous solutions having certain characteristics. For example, an aqueous solution (water) for an oral rinse may be processed having a surface tension ranging between 45 to 70 dynes per $cm^2$ producing an ORP (oxidative reduction potential) ranging between −5 m.v. to −250 m.v., preferably ranging between −10 m.v. to −125 m.v. The pH for such compositions ranges between 6.50 to 8.50, preferably 6.90 to 8.40.

The oral compositions of the present invention may be administered by any acceptable route. One typical route is the topical application as rinse, gel or paste. A further route is through application of a surgical bandage, where the composition is impregnated within the bandage.

Examples of formulations/forms for compositions of the present invention include, without limitation, the following: gels, oils, bandages/dressings, topical lotions, solutions, or drop dispersions, encapsulation in liposomes, micro-particles, enteric coatings, microcapsules, and transdermal patches.

Long-acting compositions may be administered, for example, every 8 hours or every day. Juvenile doses are generally about ½ of the adult range, depending on a variety of factors including weight and route of delivery.

The optimally effective formula and dosage(s) are adjusted (increased or decreased) as therapy progresses. A patient's saliva pH should be monitored during the treatment process and the dosage appropriately adjusted. The goal of dosage adjustment is to partially or wholly restore and maintain the physiologic optimum oral pH range between 7.0 to 7.55 and the corresponding cellular pHi above 6.40, preferably ranging between 6.41 to 6.80.

Cesium and rubidium ions used in the present are separate and distinct from man-made isotopes of cesium and rubidium.

EXAMPLES

Example 1

A sixty year old male having active periodontal (stage II and localized stage III) disease took a composition into his mouth, swished it around for approximately 20 to 30 seconds and expelled it twice daily for a period of about 2 months. The composition included cesium chloride (30 mg), rubidium chloride (10 mg), potassium citrate (350 mg) and magnesium ascorbate (20 mg) in 6 to 8 ounces of warm water. The treatment resulted in substantial suppression and elimination of the patient's periodontal disease. Inflammation and bleeding within gingival tissues were eliminated, and plaque deposits went from being moderate to very slight.

Example 2

An eighty-two year old female having ulcers on her tongue and gums the size of a dime for over a year took a composition into her mouth, swished it around for approximately 20 to 30 seconds and expelled it twice daily. The composition included CsCl (50 mg), potassium (110 mg), calcium (25 mg), magnesium (30 mg), manganese (0.5 mg) and chromium (5 mcg) in 6 to 8 ounces of warm water. After 4 days, ulceration on her tongue and gums disappeared.

Example 3

A forty-seven year old male having swollen and bleeding gums and loose teeth took a composition into his mouth, swished it around for approximately 20 to 30 seconds and expelled it twice daily. (The gum problem had persisted for more than 20 years.) The composition included cesium chloride (15 mg), rubidium chloride (5 mg), potassium citrate (175 mg) and magnesium ascorbate (10 mg) in 6 to 8 ounces of warm water. After 4 days, the patient could reinsert a dental bridge that had been previously uninsertable; after 8 days, all gum swelling, gum bleeding and tooth looseness disappeared. (Testing saliva pH pretreatment resulted in a reading of 5.9; it was between 7.1 and 7.2 seven days post treatment.)

The invention claimed is:

1. A method for improving oral hygiene in a mammal, wherein the method comprises the following steps: (a) taking a volume of a solution into the mammal's mouth, wherein the solution consists of a cesium salt, and wherein the cesium salt is selected from a group consisting of cesium arginate, cesium ascorbate, cesium caprylate, cesium cysteinate, cesium fumarate, cesium humate, cesium fulvate, cesium methionate, cesium glutamate, cesium gluconate, cesium glycinate, cesium aspartate, cesium lysinate, cesium succinate, cesium carbonate, cesium lactate, cesium malate, cesium tartrate, cesium chloride, cesium sulfate, cesium phosphate, cesium nitrate, cesium bromide, cesium iodide, and cesium orotate, water, one or more electrolytes, and said solution has a pH ranging from 7.00 to 9.70; (b) swishing the solution around; and, (c) expelling the solution thereby improving the mammal's oral hygiene.

2. The method according to claim 1, wherein the electrolyte is selected from a group of electrolytes consisting of: sodium, potassium, bicarbonate, sulfate and phosphate.

3. The method according to claim 1, wherein the cesium salt is selected from a group consisting of: cesium carbonate, cesium lactate, cesium tartrate, cesium chloride, and cesium sulfate.

4. A method for improving oral hygiene in a mammal, wherein the method comprises the following steps: (a) taking a volume of a solution into the mammal's mouth, wherein the solution consists of a cesium salt, and wherein the cesium salt is selected from a group consisting of cesium arginate, cesium ascorbate, cesium caprylate, cesium cysteinate, cesium fumarate, cesium humate, cesium fulvate, cesium methionate, cesium glutamate, cesium gluconate, cesium glycinate, cesium aspartate, cesium lysinate, cesium succinate, cesium carbonate, cesium lactate, cesium malate, cesium tartrate, cesium chloride, cesium sulfate, cesium phosphate, cesium nitrate, cesium bromide, cesium iodide, and cesium orotate; water, one or more electrolytes, and a flavorant, and said solution has a pH ranging from 7.00 to 9.7; (b) swishing the solution around; and (c) expelling the solution thereby improving the mammal's oral hygiene.

5. The method according to claim 4, wherein the cesium salt is selected from a group consisting of: cesium carbonate, cesium lactate, cesium tartrate, cesium chloride, and cesium sulfate.

6. The method according to claim 4, wherein the electrolyte is selected from the group of electrolytes consisting of: sodium, potassium, bicarbonate, sulfate and phosphate.

* * * * *